(12) United States Patent
Bruder et al.

(10) Patent No.: US 7,313,214 B2
(45) Date of Patent: Dec. 25, 2007

(54) COMPUTED TOMOGRAPHY UNIT HAVING AN APERTURE STOP

(75) Inventors: Herbert Bruder, Hoechstadt (DE); Thomas Flohr, Uehlfeld (DE); Karl Stierstorfer, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 126 days.

(21) Appl. No.: 11/100,531

(22) Filed: Apr. 7, 2005

(65) Prior Publication Data

US 2005/0232390 A1 Oct. 20, 2005

(30) Foreign Application Priority Data

Apr. 8, 2004 (DE) .................. 10 2004 017 538

(51) Int. Cl.
*A61B 6/03* (2006.01)
*G01N 23/083* (2006.01)

(52) U.S. Cl. .................. 378/15; 378/7; 378/9

(58) Field of Classification Search .......... 378/7, 378/9, 15
See application file for complete search history.

(56) References Cited

U.S. PATENT DOCUMENTS

| | | | |
|---|---|---|---|
| 4,637,040 A * | 1/1987 | Sohval et al. .................. | 378/9 |
| 5,142,286 A * | 8/1992 | Ribner et al. ................ | 341/143 |
| 5,361,291 A * | 11/1994 | Toth et al. ..................... | 378/12 |
| 5,625,661 A | 4/1997 | Oikawa | |
| 6,256,369 B1 * | 7/2001 | Lai .............................. | 378/14 |
| 6,272,199 B1 | 8/2001 | Sembritzki et al. | |
| 6,483,890 B1 * | 11/2002 | Malamud ..................... | 378/22 |

FOREIGN PATENT DOCUMENTS

| | | |
|---|---|---|
| DE | 198 51 556 A1 | 5/2000 |
| DE | 299 23 967 U1 | 10/2001 |
| DE | 102 01 321 A1 | 7/2003 |
| DE | 102 11 948 A1 | 10/2003 |

OTHER PUBLICATIONS

"Bildgebende Systeme für die medizinische Diagnostik", Kap. 2.2.3, Herausgeber: Heinz Morneburg, 3. Auflage, ISBN 89578-002-2, Seiten 55-58.
German Office Action dated Jan. 13, 2005.

* cited by examiner

*Primary Examiner*—Edward J. Glick
*Assistant Examiner*—Thomas R. Artman
(74) *Attorney, Agent, or Firm*—Harness, Dickey & Pierce, P.L.C.

(57) ABSTRACT

A computed tomography unit includes at least one X-ray tube, that scans an object in a fashion rotating in a circle or spiral about a z-axis, in combination with an oppositely situated detector having a multiplicity of detector rows. Each detector row includes an aperture $\Delta z$ in the z-direction, having a multiplicity of detector elements. Between the X-ray tube and detector, a detector diaphragm is arranged that reduces the aperture $\Delta z$ of the detector rows in the z-direction. The X-ray tube includes a focus, of variable location relative to the X-ray tube and which alternatingly assumes during scanning at least two different positions that have different z-coordinates relative to the X-ray tube R.

14 Claims, 4 Drawing Sheets

COMPUTED TOMOGRAPHY UNIT HAVING AN APERTURE STOP

The present application hereby claims priority under 35 U.S.C. §119 on German patent application number DE 10 2004 017 538.1 filed Apr. 8, 2004, the entire contents of which is hereby incorporated herein by reference.

FIELD OF THE INVENTION

The invention generally relates to a computed tomography unit having at least one X-ray tube. Preferably it relates to such a unit which scans an object, in a fashion rotating in a circle or spiral about a z-axis, in combination with an oppositely situated detector having a multiplicity of detector rows. Each detector row may include an aperture Δz in the z-direction, having a multiplicity of detector elements. Furthermore, being arranged between the X-ray tube and detector, there may be a detector diaphragm that reduces the aperture Δz of the detector rows in the z-direction.

BACKGROUND OF THE INVENTION

German laid-open patent application DE 102 11 948 A1 has disclosed a computed tomography unit that is equipped with an X-ray tube with a fixed focus and has, situated opposite, a multirow detector that is equipped in a first variant (FIG. 3) with a so-called z-comb that acts as an aperture stop in the z-direction for the detector rows. In a second variant (FIG. 4), the laid-open patent application discloses a detector diaphragm that, in addition to the aperture stop in the z-direction, also has an aperture stop in the circumferential direction or longitudinal direction of the detector. Thus, the active cross sections of the individual detector elements are constricted from all sides such that their aperture is reduced in two dimensions.

Fundamentally, such a reduction in the active cross-sectional surface takes place in order to improve the resolution of the detector. However, a reduction in the cross-sectional surface is simultaneously attended by a reduction in the sensitivity of the detector and leads—at least in the case of human diagnosis—to an undesired increase in the radiation burden such that limits are set for the reduction in the aperture by the reduction in the sensitivity of the detector.

SUMMARY OF THE INVENTION

It is an object of an embodiment of the invention to find a computed tomography unit having a multirow detector and which has an improved resolution, without the need to increase the radiation dose used.

The inventors have realized that an increase in the longitudinal resolution, that is to say the resolution in the direction of the z-axis or the system axis, both undesirably increases the required radiation dose, and leads to an enlargement, likewise undesired, of the dead spaces between the active radiation areas. Again, the cutoff frequency, thereby increased, of the spatial frequency $f(z)=1/a_{Kamm}$, where $a_{Kamm}$ is the open width of the aperture stop (z-comb) in the z-direction, cannot actually be used, since the Nyquist frequency lies unchanged in the vicinity of $1/(2*a)$, where a is the opening of the aperture stop, and aliasing artifacts thereby arise.

This problem can, however, be circumvented when the scanning rate is raised. This can be done, for example, by virtue of the fact that a flying focus is used that alternately flies to two or more positions in the z-direction, that is to say with different z-coordinates with reference to the X-ray tube.

The inventors consequently propose, in at least one embodiment, a computed tomography unit including at least one X-ray tube that scans an object, in a fashion rotating in a circle or spiral about a z-axis, in combination with an oppositely situated detector having a multiplicity of detector rows. Each detector row may include an aperture Δz in the z-direction, having a multiplicity of detector elements. Further, between the X-ray tube and detector, a detector diaphragm may be arranged that reduces the aperture Δz of the detector rows in the z-direction, to the effect that the X-ray tube has a focus of variable location relative to the X-ray tube and which alternatingly assumes during scanning at least two different positions that have different z-coordinates relative to the X-ray tube.

The result of this configuration is that the scanning rate may be multiplied in accordance with a number of different positions of the flying focus in the z-direction. Thus, the useful range of longitudinal spatial frequencies may thereby be enlarged.

The inventors also propose, in at least one embodiment, that at least two different positions of the focus additionally have different coordinates relative to the X-ray tube in the circumferential direction. This refinement then additionally also permits the scanning rate to be raised in the circumferential direction or longitudinal direction of the detector in accordance with the number of different positions of the flying focus in the circumferential direction, and thus an enlargement of the useful range of the spatial frequencies in the circumferential direction.

A further improvement of the resolution in the circumferential direction in at least one embodiment may be achieved when the aperture stop of the detector is also designed in the case of the computed tomography unit, such that it cuts the active surface of the individual detector elements in the circumferential direction.

For example, the aperture stop of the detector can be designed such that the active surface of the individual detector elements is of square design.

If use is made of a computed tomography unit that has a variable gantry feed rate relative to the examination object, it is possible according to at least one embodiment of the invention to configure the control device for the positions flown to by the flying focus such that the control device that varies the spacings of the flying focal position in the z-direction as a function of the selected feed of the X-ray tube and detector. It is then particularly advantageous in this case, when the spacings of the flying focus positions are proportional to the feed of the X-ray tube and detector. Thus, given a relatively small feed a closer spacing of the individual flying focus positions is also simultaneously selected so that the examination object is covered as uniformly as possible with beam paths. The spacings of the flying focus can be enlarged correspondingly when the feed is enlarged.

BRIEF DESCRIPTION OF THE DRAWINGS

Example embodiments of the invention are explained below in more detail with the aid of the figures, in which it may be noted that only the elements central to an immediate understanding of embodiments of the invention are shown. The following reference symbols are used in the process: 1: profile of the transfer function with out aperture stop; 2: profile of the transfer function with aperture stop; I: useful spatial frequency range without aperture stop; II: additionally useful spatial frequency range with aperture stop; III.

useful spatial frequency range with aperture stop and flying focus having two positions; a: aperture of a detector row of a multirow detector without aperture stop in the z-direction; $a_{Kamm}$: aperture of an aperture stop of a multirow detector in the z-direction; b: period width/grid width of the detector rows of a multirow detector without aperture stop in the z-direction; d: spacing between the detector elements of two rows; $f_z$: spatial frequency in the z-direction; A: aperture stop; B: examination object; C: computer; D: detector; E: detector elements; $F_n$: focus positions; L: length of the detector in the row/circumferential direction; H: width of the detector in the z-direction; M: monitor; $P_n$: programs/program modules; Q: surface perpendicular to the central beam; R: X-ray tube; S: X-rays; $S_z$: central beam; U(f): transfer function; z: system axis/z-axis. In detail.

DETAILED DESCRIPTION OF THE EXAMPLE EMBODIMENTS

Figure 1:
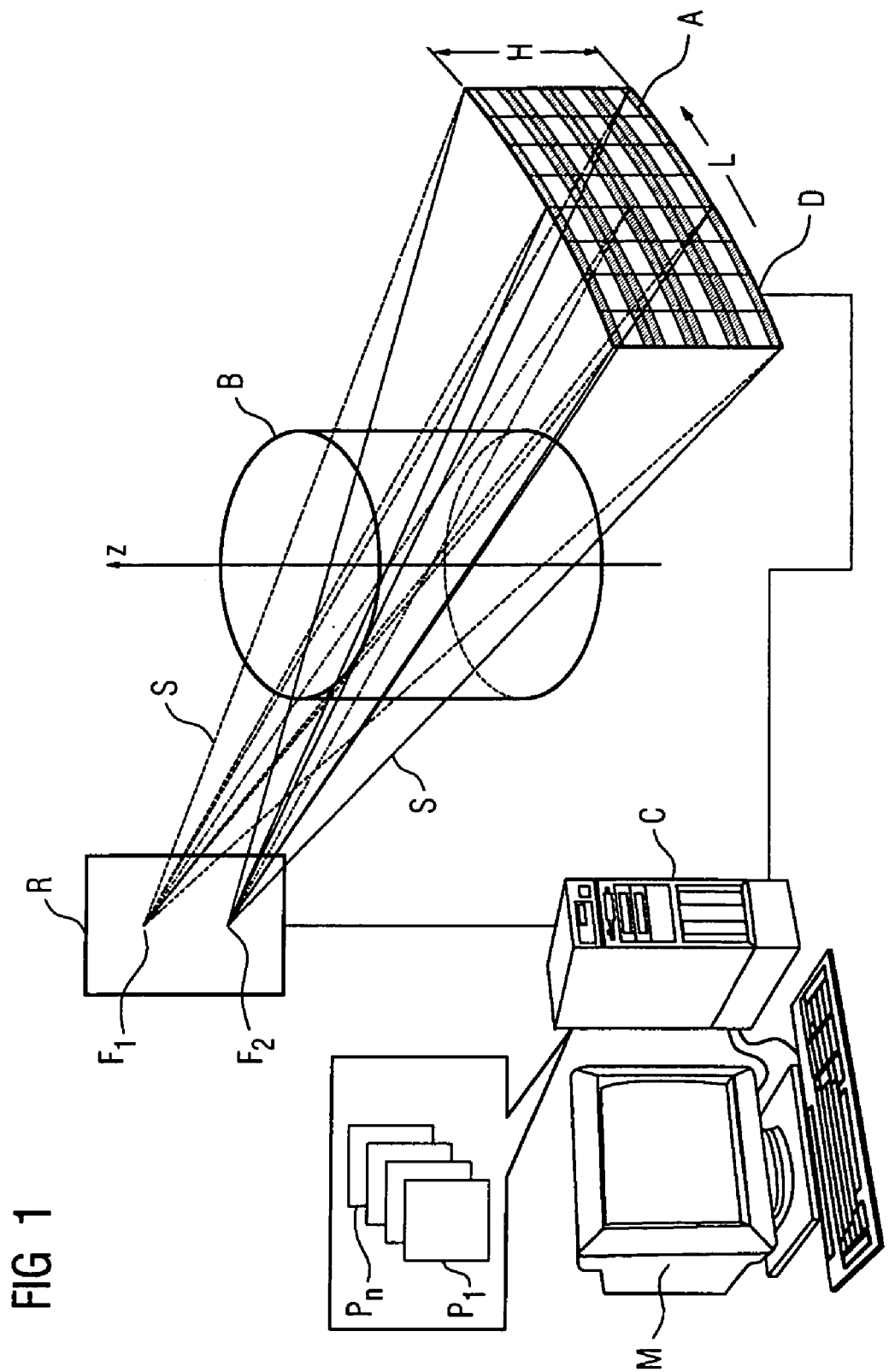
FIG. 1: shows a schematic of a CT having a flying focus in the z-direction and an aperture stop at the multirow detector in the z-direction.

FIG. 1 shows a schematic of a computed tomography unit according to an embodiment of the invention and having a flying focus with two flying focus positions $F_1$ and $F_2$ that in each case emit beams S onto a detector D and in the process penetrate an examination object B, the attenuation of their radiation being measured by the detector D. The detector D has a length L in the circumferential direction and a width H in the z-direction and is divided into a multiplicity of detector rows that consist, in turn, of individual detector elements, there being placed over the individual detector rows, in the example shown, an aperture stop that acts exclusively in the z-direction. The control of the focus positions and the picking up of the data from the detector are performed via a computer unit C that has appropriate programs $P_n$ for control including driving the flying focus positions, data pickup for the detector, data conditioning to form the CT image and for carrying out the method according to an embodiment of the invention.

Figure 2:
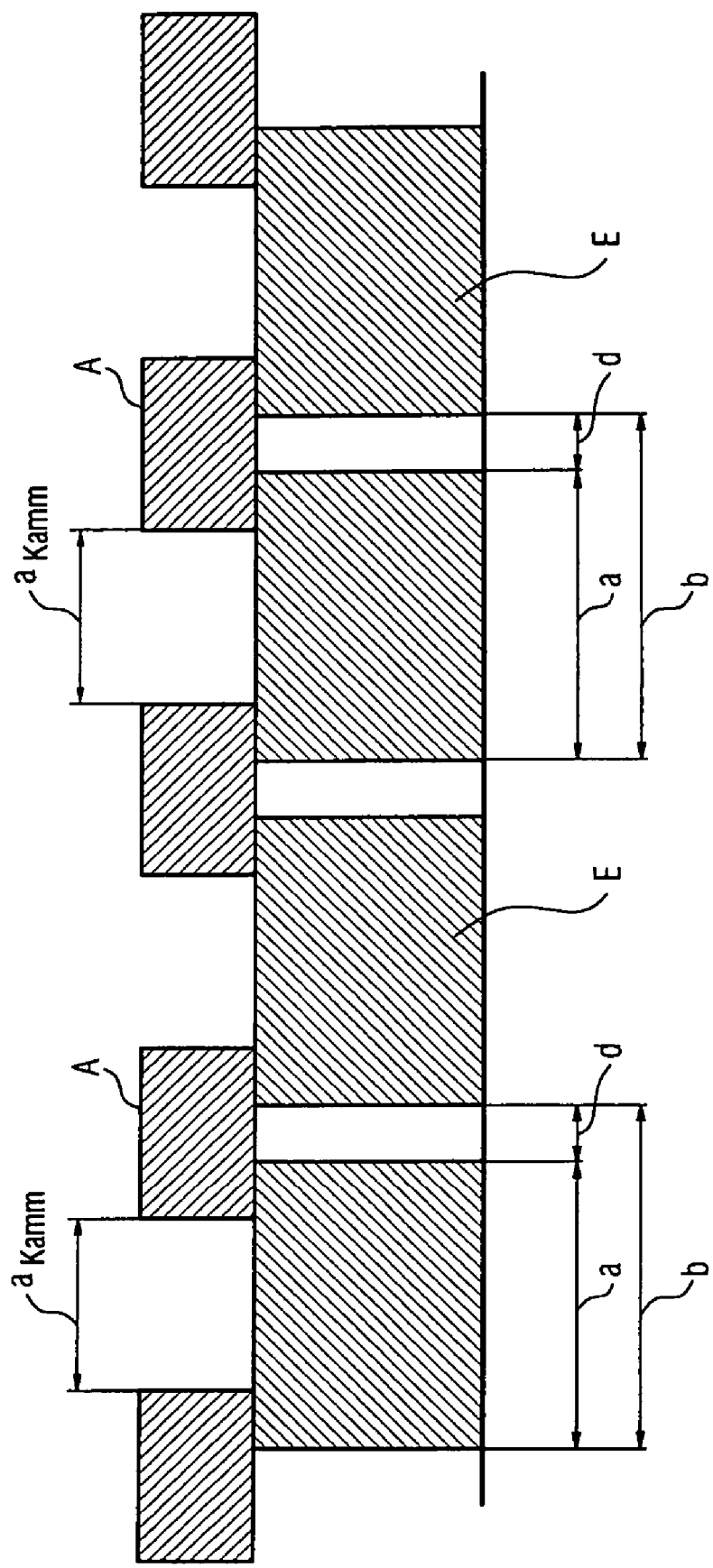
FIG. 2: shows a section in the z-direction through a multirow detector.
Figure 3:
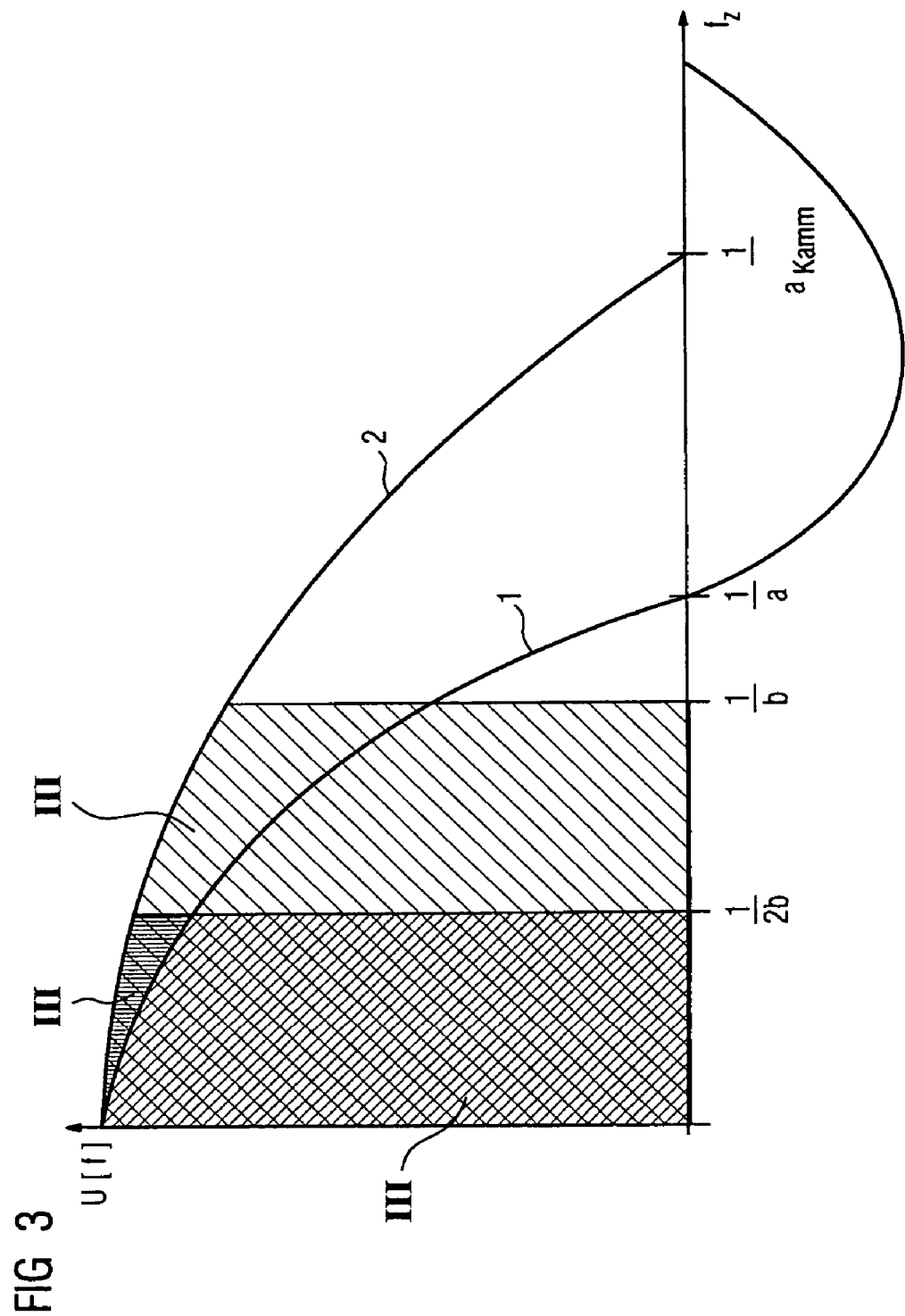
FIG. 3: shows a graph of the transfer functions as a function of the spatial frequency with and without a flying focus.

The basic idea of the method according to an embodiment of the invention is illustrated schematically in FIGS. 2 and 3 by illustrating the transfer functions U(f) in a fashion plotted against the longitudinal spatial frequency $f_z$.

FIG. 2 shows a section through a multirow detector in the z-direction, a total of 4 detector elements E from 4 rows of the detector D being illustrated. The individual detector elements have a mutual spacing "d" and a width "a" that corresponds to the aperture without an aperture stop. The grid width of the detector rows, or their period, results from the sum of the width a and the spacing d, where b=a+d. Arranged above the detector element E is an aperture stop A that has per row an opening width or aperture $a_{Kamm}$ and limits the active surface of the detector elements to this width.

FIG. 3 shows the graph 1 of the transfer function U(f) for the case of a focus detector system having a single, non-flying focus and an aperture a of the detector. The aperture "a" determines the frequency response such that the transfer function cuts the abscissa to the value 1/a. However, at the same time the grid width b of the multirow detector limits the sampling properties by the Nyquist condition such that the actually useful spatial frequency range is reduced by the hatched area I to the left of 1/2b.

By contrast, the graph 2 illustrates the transfer function of the same detector—but with an aperture stop having the reduced aperture $a_{Kamm}$. In conjunction with the same limitation by the Nyquist condition, the result in this case is a gain in the transfer function by comparison with the detector without an aperture stop, as illustrated in the area II. If, by contrast, the Nyquist condition or its bound is displaced to higher frequencies by superimposing on the simple sample one or more further spatially displaced samples, as is the case with a flying focus system. This results in a large additional gain with reference to the transfer function, as illustrated by the area III. Since it holds for the transfer function that the pictorial reproduction is better the larger the value of the transfer function U(f), this results correspondingly in a substantially higher resolution owing to the combination of flying focus and aperture stop.

Thus, it appears initially upon a superficial consideration that as the aperture becomes arbitrarily smaller, it is also possible to sample arbitrarily small spatial frequencies. However, on the basis of the maximum resolvable spatial frequency in accordance with the Nyquist condition for the sampling of analog signals, and of the recovery of analog signals from discrete values, the latter turns out to be a substantial limiting factor. Reference may be made, for example, to "Bildgebende Systeme für die medizinische Diagnostik" ["Imaging systems for medical diagnostics"], chapter 2.2.3, publisher Heinz Morneburg, 3rd edition, ISBN 89578-002-2 regarding the derivation of the theoretical background of the Nyquist condition, the entire contents of which are hereby incorporated herein by reference.

Thus, if use is made in the way according to an embodiment of the invention of a combination of a flying focal system with increased sampling density—FIG. 3 shows the situation with two flying focus positions such that the sampling density grows from b to b/2—with an additional aperture stop, this results, on the one hand, in a displacement of the limiting Nyquist frequency to double the frequency value from 1/2b to 1/b and, at the same time, in a stretching of the graph 2 by comparison with the profile of the graph 1 for the transfer function U(f), because of the additionally used aperture stop with the smaller aperture $1/a_{Kamm}$ by comparison with the graph 1 having the aperture a.

It may be pointed out that additional improvements by comparison with the example illustrated are possible by using a flying focus with a further increased number of flying focus positions in the direction respectively considered. In particular, in addition to a number of flying focus positions in the z-direction, it can be advantageous also to vary the flying focus position in the circumferential direction of the X-ray tube, since this also improves the resolving power of the detector elements in the circumferential direction or longitudinal direction of the detector, this taking place with particular advantage in a combination with an additional aperture stop of the detector elements in the circumferential direction, corresponding to the previously outlined basic idea in the z-direction.

Figure 4:
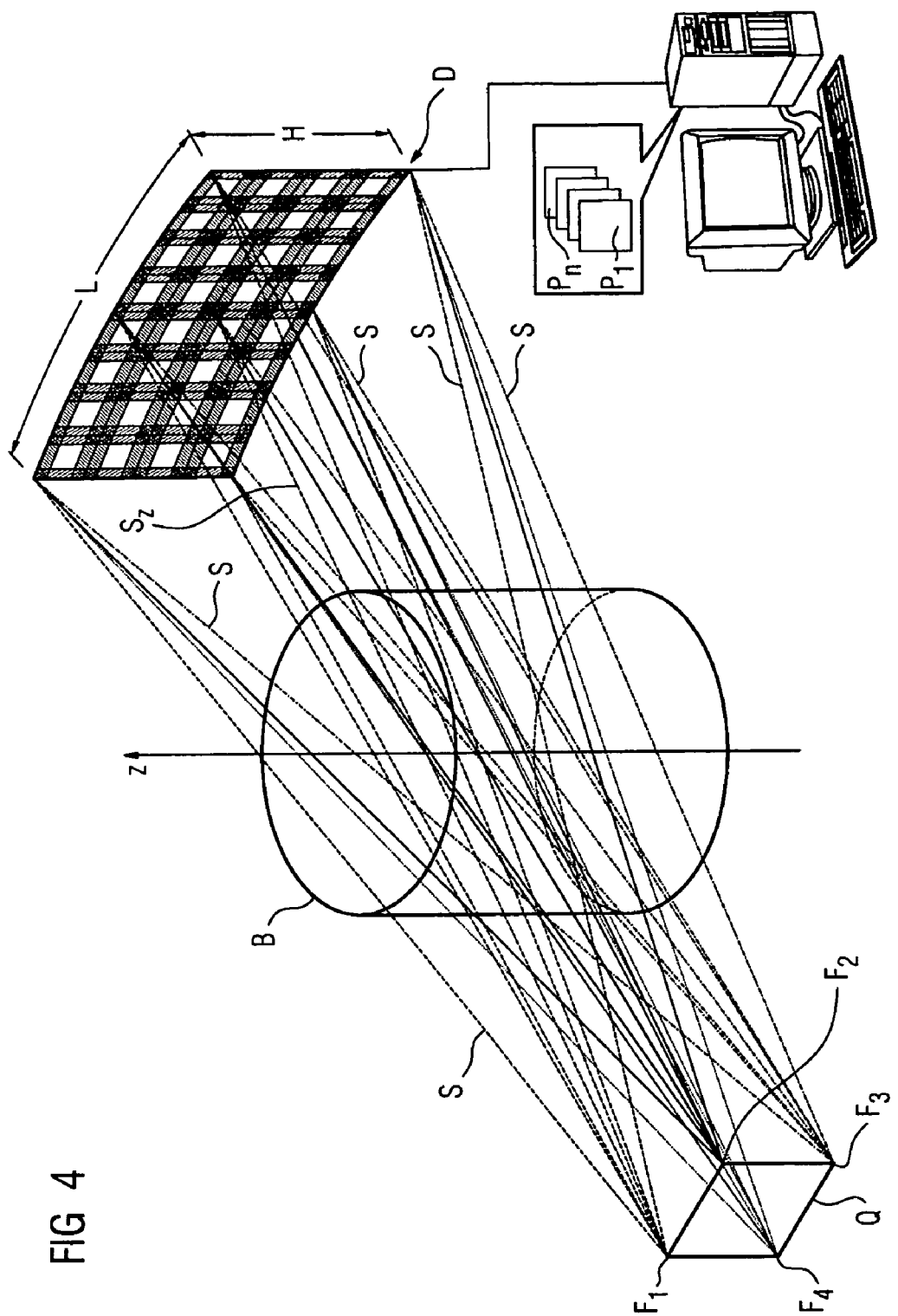
FIG. 4: shows a schematic of a CT having a flying focus in the z-direction and circumferential direction including an aperture stop at the multirow detector in the z- and circumferential directions.

FIG. 4 shows for this purpose an exemplary and schematic illustration of such a focus detector system with four flying focus positions $F_1$ to $F_4$ in conjunction with a detector element D that has an aperture stop which reduces the individual detector elements both in the z-direction and in the circumferential direction with reference to their open surface. The four flying focus positions are arranged at the corners of a rectangle Q that bears tangentially against the circumferential plane of the X-ray tube around the examination object B.

The result of this arrangement of the four focus positions is to double the scanning frequency both in the z-direction and in the circumferential direction in a way according to an embodiment of the invention such that in conjunction with the simultaneously reduced aperture in the z-direction and circumferential direction of the detector. The desired improvement of the transfer function of the spatial frequencies is yielded both in the z-direction and in the circumferential direction or longitudinal direction of the detector.

An embodiment of the invention therefore proposes selecting a combination of a flying focus system having a multirow detector and aperture stop at least in the z-direction, the result of this being both an improved spatial transfer function and a raising of the resolution-limiting Nyquist frequency.

It is self-evident that the abovementioned features of an embodiment of the invention can be used not only in the combination respectively specified, but also in other combinations or alone, without departing from the scope of the invention. It is self-evident, furthermore, that a CT unit within the meaning of the invention is to be understood not only as the classic X-ray computed tomography unit with a closed gantry but also other units, including for example so-called C-arc units.

Exemplary embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A computed tomography unit, comprising:
   at least one X-ray tube, adapted to scan an object in a fashion rotating in a circle or spiral about a z-axis;
   a detector, oppositely situated to the at least one X-ray tube and including a multiplicity of detector rows, each detector row having an aperture $\Delta z$ in the z-direction and having a multiplicity of detector elements; and
   a detector diaphragm, arranged between the at least one X-ray tube and the detector, adapted to reduce the aperture $\Delta z$ of the detector rows in the z-direction, the X-ray tube including a focus of variable location relative to the X-ray tube and which alternatingly assumes during sampling at least two different positions that have different z-coordinates relative to the X-ray tube, a scanning rate in the z-direction being multiplied in accordance with the number of the different z-coordinates of the focus in relation to the X-ray tube; wherein the detector diaphragm is designed such that it cuts the active surface of the individual detector elements in the circumferential direction, and
   the detector diaphragm is designed such that the active surface of the individual detector elements is of square design.

2. A computed tomography unit, comprising:
   at least one X-ray tube, adapted to scan an object in a fashion rotating in a circle or spiral about a z-axis;
   a detector, oppositely situated to the at least one X-ray tube and including a multiplicity of detector rows, each detector row having an aperture $\Delta z$ in the z-direction and having a multiplicity of detector elements; and
   a detector diaphragm, arranged between the at least one X-ray tube and the detector, adapted to reduce the aperture $\Delta z$ of the detector rows in the z-direction, the X-ray tube including a focus of variable location relative to the X-ray tube and which alternatingly assumes during sampling at least two different positions that have different z-coordinates relative to the X-ray tube, a scanning rate in the z-direction being multiplied in accordance with the number of the different z-coordinates of the focus in relation to the X-ray tube; wherein for the positions flown to by a flying focus, a control device is provided that varies the spacings of a flying focal position in the z-direction as a function of a selected feed of the X-ray tube and detector.

3. The computed tomography unit as claimed in claim 2, wherein the at least two different positions of focus additionally have different coordinates relative to the X-ray tube in the circumferential direction.

4. The computed tomography unit as claimed in claim 3, wherein the detector diaphragm is designed such that it cuts the active surface of the individual detector elements in the circumferential direction.

5. The computed tomography unit as claimed in claim 2, wherein spacings of the flying focal positions are proportional to the feed of the X-ray tube and detector.

6. A computed tomography unit, comprising:
   at least one X-ray tube, adapted to scan an object in a fashion rotating in a circle or spiral about a z-axis;
   a detector, oppositely situated to the at least one X-ray tube and including a multiplicity of detector rows, each detector row having an aperture $\Delta z$ in the z-direction and having a multiplicity of detector elements; and
   a detector diaphragm, arranged between the at least one X-ray tube and the detector, adapted to reduce the aperture $\Delta z$ of the detector rows in the z-direction, the X-ray tube including a focus of variable location relative to the X-ray tube and which alternatingly assumes during sampling at least two different positions that have different z-coordinates relative to the X-ray tube, a scanning rate in the z-direction being multiplied in accordance with the number of the different z-coordinates of the focus in relation to the X-ray tube; wherein the detector diaphragm is designed such that it cuts the active surface of the individual detector elements in the circumferential direction, and
   the detector diaphragm is designed such that the active surface of the individual detector elements is of square design.

7. The computed tomography unit as claimed in claim 6, wherein, for the positions flown to by a flying focus, a control device is provided that varies the spacings of a flying focal position in the z-direction as a function of a selected feed of the X-ray tube and detector.

8. The computed tomography unit as claimed in claim 7, wherein spacings of the flying focal positions are proportional to the feed of the X-ray tube and detector.

9. A computed tomography unit, comprising:
   at least one X-ray tube, adapted to scan an object in a fashion rotating in a circle or spiral about a z-axis;
   a detector, oppositely situated to the at least one X-ray tube and including a multiplicity of detector rows, each detector row having an aperture $\Delta z$ in the z-direction and having a multiplicity of detector elements; and
   a detector diaphragm, arranged between the at least one X-ray tube and the detector, adapted to reduce the aperture $\Delta z$ of the detector rows in the z-direction, the X-ray tube including a focus of variable location relative to the X-ray tube and which alternatingly assumes during sampling at least two different positions that have different z-coordinates relative to the X-ray tube, a scanning rate in the z-direction being multiplied in accordance with the number of the different z-coordinates of the focus in relation to the X-ray tube; wherein
the at least two different positions of focus additionally have different coordinates relative to the X-ray tube in the circumferential direction, and
for the positions flown to by a flying focus, a control device is provided that varies the spacings of a flying focal position in the z-direction as a function of a selected feed of the X-ray tube and detector.

10. The computed tomography unit as claimed in claim 9, wherein spacings of the flying focal positions are proportional to the feed of the X-ray tube and detector.

11. A computed tomography unit, comprising:
at least one X-ray tube, adapted to scan an object in a fashion rotating in a circle or spiral about a z-axis;
a detector, oppositely situated to the at least one X-ray tube and including a multiplicity of detector rows, each detector row having an aperture $\Delta z$ in the z-direction and having a multiplicity of detector elements; and
a detector diaphragm, arranged between the at least one X-ray tube and the detector, adapted to reduce the aperture $\Delta z$ of the detector rows in the z-direction, the X-ray tube including a focus of variable location relative to the X-ray tube and which alternatingly assumes during sampling at least two different positions that have different z-coordinates relative to the X-ray tube, a scanning rate in the z-direction being multiplied in accordance with the number of the different z-coordinates of the focus in relation to the X-ray tube; wherein
the detector diaphragm is designed such that it cuts the active surface of the individual detector elements in the circumferential direction, and
for the positions flown to by a flying focus, a control device is provided that varies the spacings of a flying focal position in the z-direction as a function of a selected feed of the X-ray tube and detector.

12. The computed tomography unit as claimed in claim 11, wherein spacings of the flying focal positions are proportional to the feed of the X-ray tube and detector.

13. A computed tomography unit, comprising:
at least one X-ray tube, adapted to scan an object in a fashion rotating in a circle or spiral about a z-axis;
a detector, oppositely situated to the at least one X-ray tube and including a multiplicity of detector rows, each detector row having an aperture $\Delta z$ in the z-direction and having a multiplicity of detector elements; and
a detector diaphragm, arranged between the at least one X-ray tube and the detector, adapted to reduce the aperture $\Delta z$ of the detector rows in the z-direction, the X-ray tube including a focus of variable location relative to the X-ray tube and which alternatingly assumes during sampling at least two different positions that have different z-coordinates relative to the X-ray tube, a scanning rate in the z-direction being multiplied in accordance with the number of the different z-coordinates of the focus in relation to the X-ray tube; wherein
the detector diaphragm is designed such that it cuts the active surface of the individual detector elements in the circumferential direction,
the detector diaphragm is designed such that the active surface of the individual detector elements is of square design, and
for the positions flown to by a flying focus, a control device is provided that varies the spacings of a flying focal position in the z-direction as a function of a selected feed of the X-ray tube and detector.

14. The computed tomography unit as claimed in claim 13, wherein spacings of the flying focal positions are proportional to the feed of the X-ray tube and detector.

* * * * *